(12) United States Patent  
Dobrin et al.

(10) Patent No.: US 7,581,273 B2
(45) Date of Patent: *Sep. 1, 2009

(54) DISPOSABLE NONWOVEN CLEANSING MITT

(75) Inventors: George Christopher Dobrin, Mason, OH (US); Teresa Lynne Horton, Cincinnati, OH (US); Michael Wayne Mason, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/797,423

(22) Filed: Mar. 10, 2004

(65) Prior Publication Data

US 2004/0204333 A1    Oct. 14, 2004

Related U.S. Application Data

(60) Provisional application No. 60/453,160, filed on Mar. 10, 2003.

(51) Int. Cl.
*A47L 13/19* (2006.01)
*A47K 7/03* (2006.01)

(52) U.S. Cl. .................. 15/104.94; 15/227; 15/210.1; 401/7

(58) Field of Classification Search .............. 15/227, 15/104.93, 104.94, 229.13, 209.1, 210.1, 15/118, 208, 244.1, 244.2; 401/7; 2/158; 424/443

See application file for complete search history.

(56) References Cited

U.S. PATENT DOCUMENTS

| | | | |
|---|---|---|---|
| 1,547,179 A | 7/1925 | Martens | |
| 2,798,053 A | 7/1957 | Brown | |
| 2,831,854 A | 4/1958 | Tucker et al. | |
| 3,711,889 A | 1/1973 | Jennings | |
| 3,755,560 A | 8/1973 | Dickert et al. | |
| 3,862,472 A | 1/1975 | Norton et al. | |
| 3,902,509 A | 9/1975 | Tundermann et al. | |
| 3,929,678 A | 12/1975 | Laughlin et al. | |
| 3,963,699 A | 6/1976 | Rizzi et al. | |
| 3,967,756 A | 7/1976 | Barish | |
| 3,982,302 A | 9/1976 | Vaalburg | |
| 3,982,659 A | 9/1976 | Ross | |
| 3,986,479 A | 10/1976 | Boedecker | |
| 3,994,417 A | 11/1976 | Boedecker | |
| 4,004,323 A | 1/1977 | Gotchel | |
| 4,005,195 A | 1/1977 | Jandacek | |
| 4,005,196 A | 1/1977 | Jandacek | |
| 4,057,669 A | 11/1977 | McConnell | |
| 4,097,965 A | 7/1978 | Gotchel | |

(Continued)

FOREIGN PATENT DOCUMENTS

EP    0068516 A1    1/1983

(Continued)

OTHER PUBLICATIONS

US 5,305,514, 04/1994, Letton et al. (withdrawn)

*Primary Examiner*—Gary K Graham
(74) *Attorney, Agent, or Firm*—Sarah Ann Dressel; John G. Powell

(57) ABSTRACT

A disposable nonwoven cleansing mitt adapted to fit on a user's hand, such as a child, is provided. The disposable nonwoven cleansing mitt releasably contains a personal care composition.

13 Claims, 8 Drawing Sheets

U.S. PATENT DOCUMENTS

| | | | |
|---|---|---|---|
| 4,130,915 A | 12/1978 | Gotchel | |
| 4,135,024 A | 1/1979 | Callahan | |
| 4,154,542 A * | 5/1979 | Rasmason | 401/7 |
| 4,176,427 A | 12/1979 | Neuenschwander | |
| 4,189,896 A | 2/1980 | Kolbach | |
| 4,207,367 A | 6/1980 | Baker, Jr. | |
| 4,233,212 A | 11/1980 | Otoi et al. | |
| 4,296,161 A | 10/1981 | Kaiser | |
| 4,309,469 A | 1/1982 | Varona | |
| 4,421,769 A | 12/1983 | Dixon et al. | |
| 4,471,881 A | 9/1984 | Foster | |
| 4,509,949 A | 4/1985 | Huang et al. | |
| 4,517,360 A | 5/1985 | Volpenhein | |
| 4,518,772 A | 5/1985 | Volpenhein | |
| 4,523,348 A | 6/1985 | Petrie | |
| 4,599,379 A | 7/1986 | Flesher et al. | |
| 4,628,078 A | 12/1986 | Glover et al. | |
| 4,637,859 A | 1/1987 | Trokhan | |
| 4,682,942 A | 7/1987 | Gotchel | |
| 4,741,855 A | 5/1988 | Grote et al. | |
| 4,797,300 A | 1/1989 | Jandacek et al. | |
| 4,835,206 A | 5/1989 | Farrar et al. | |
| 4,839,165 A | 6/1989 | Hoppe et al. | |
| 4,839,168 A | 6/1989 | Abe et al. | |
| 4,840,270 A | 6/1989 | Caputo | |
| 4,849,484 A | 7/1989 | Heard | |
| 4,893,372 A | 1/1990 | Wenzel | |
| 4,960,764 A | 10/1990 | Figueroa, Jr. et al. | |
| 4,971,220 A | 11/1990 | Kaufman | |
| 4,976,953 A | 12/1990 | Orr et al. | |
| 5,009,813 A | 4/1991 | Watanabe et al. | |
| 5,050,737 A | 9/1991 | Joslyin | |
| 5,069,898 A | 12/1991 | Goldberg | |
| 5,087,445 A | 2/1992 | Haffey et al. | |
| 5,100,660 A | 3/1992 | Hawe et al. | |
| 5,223,096 A | 6/1993 | Phan | |
| 5,240,562 A | 8/1993 | Phan | |
| 5,306,514 A | 4/1994 | Letton et al. | |
| 5,306,515 A | 4/1994 | Letton et al. | |
| 5,306,516 A | 4/1994 | Letton et al. | |
| 5,322,178 A | 6/1994 | Foos | |
| 5,366,104 A | 11/1994 | Armstrong | |
| 5,412,634 A | 5/1995 | Buchler et al. | |
| 5,412,830 A * | 5/1995 | Girardot et al. | 15/118 |
| 5,487,884 A | 1/1996 | Bissett et al. | |
| 5,540,976 A * | 7/1996 | Shawver et al. | 428/198 |
| 5,542,566 A | 8/1996 | Glaug | |
| 5,556,509 A | 9/1996 | Trokhan | |
| 5,580,423 A | 12/1996 | Ampulski | |
| 5,605,749 A * | 2/1997 | Pike et al. | 442/60 |
| 5,607,980 A | 3/1997 | McAtee et al. | |
| 5,647,506 A | 7/1997 | Julius | |
| 5,649,336 A | 7/1997 | Finch | |
| 5,686,082 A | 11/1997 | N'Guyen | |
| 5,725,382 A | 3/1998 | Walter et al. | |
| 5,785,179 A | 7/1998 | Buczwinski | |
| 5,791,465 A | 8/1998 | Niki | |
| 5,839,842 A | 11/1998 | Wanat et al. | |
| 5,883,998 A | 11/1998 | Biederman et al. | |
| 5,939,082 A | 8/1999 | Oblong et al. | |
| 5,955,417 A * | 9/1999 | Taylor | 510/438 |
| D414,637 S | 10/1999 | Amundson | |
| D416,794 S | 11/1999 | Cormack | |
| 6,024,970 A | 2/2000 | Woodard | |
| D421,901 S | 3/2000 | Hill | |
| D421,902 S | 3/2000 | Hill | |
| 6,092,690 A | 7/2000 | Bitowft | |
| D437,686 S | 2/2001 | Balzar | |
| 6,200,554 B1 | 3/2001 | Yeoh et al. | |
| 6,206,863 B1 * | 3/2001 | Skewes et al. | 604/290 |
| 6,238,678 B1 | 5/2001 | Oblong et al. | |
| D443,451 S | 6/2001 | Buck | |
| D443,508 S | 6/2001 | Braaten | |
| 6,248,317 B1 | 6/2001 | Snyder et al. | |
| D445,329 S | 7/2001 | Zethoff | |
| 6,257,785 B1 | 7/2001 | Otten | |
| 6,269,969 B1 | 8/2001 | Huang | |
| 6,269,970 B1 | 8/2001 | Huang | |
| 6,292,949 B1 | 9/2001 | Chang | |
| 6,296,144 B1 | 10/2001 | Tanaka | |
| 6,315,114 B1 | 11/2001 | Keck | |
| 6,322,801 B1 | 11/2001 | Lorenzi et al. | |
| D451,279 S | 12/2001 | Chin | |
| 6,335,312 B1 | 1/2002 | Coffindaffer et al. | |
| 6,401,968 B1 | 6/2002 | Huang | |
| 6,412,634 B1 | 7/2002 | Telesca | |
| 6,440,437 B1 | 8/2002 | Krzysik et al. | |
| 6,501,002 B1 | 12/2002 | Roe et al. | |
| 6,506,394 B1 | 1/2003 | Yahiaoui et al. | |
| 6,630,175 B1 | 10/2003 | Shapiro et al. | |
| 6,780,825 B2 | 8/2004 | Piterski et al. | |
| 7,021,483 B2 | 4/2006 | Tack et al. | |
| 7,152,737 B2 | 12/2006 | Chin | |
| 7,188,746 B2 | 3/2007 | Zethoff et al. | |
| 7,401,376 B2 * | 7/2008 | Benjamin et al. | 15/104.94 |
| 2002/0178482 A1 | 12/2002 | Samuelsson et al. | |
| 2003/0130636 A1 | 7/2003 | Brock et al. | |
| 2003/0140439 A1 | 7/2003 | Durden et al. | |
| 2003/0190337 A1 | 10/2003 | Bissett | |
| 2003/0215486 A1 | 11/2003 | Berry et al. | |
| 2003/0217425 A1 | 11/2003 | Datta et al. | |
| 2004/0022833 A1 | 2/2004 | Hartwig | |
| 2004/0204333 A1 | 10/2004 | Dobrin et al. | |
| 2005/0042261 A1 * | 2/2005 | Hasenoehrl et al. | 424/443 |
| 2005/0125877 A1 | 6/2005 | Benjamin et al. | |
| 2005/0125923 A1 | 6/2005 | Benjamin et al. | |
| 2005/0125924 A1 | 6/2005 | Benjamin et al. | |
| 2005/0129743 A1 | 6/2005 | Benjamin et al. | |
| 2005/0150784 A1 | 7/2005 | Sanchez et al. | |
| 2005/0220847 A1 | 10/2005 | Benjamin et al. | |

FOREIGN PATENT DOCUMENTS

| | | |
|---|---|---|
| EP | 0 228 868 A2 | 7/1987 |
| FR | 2 813 777 | 3/2002 |
| WO | WO 97/38598 A1 | 10/1997 |
| WO | WO 99/55213 A1 | 11/1999 |
| WO | WO 03/000106 A1 | 1/2003 |

* cited by examiner

DISPOSABLE NONWOVEN CLEANSING MITT

CROSS REFERENCE TO RELATED APPLICATION

This application claims the benefit of U.S. Provisional Application No. 60/453,160, filed on Mar. 10, 2003.

FIELD OF INVENTION

A disposable nonwoven cleansing mitt adapted to fit on a user's hand is provided. The disposable nonwoven cleansing mitt is releasably carrying a personal care composition.

BACKGROUND OF THE INVENTION

Personal care products, particularly cleansing and conditioning products, have traditionally been marketed in a variety of forms such as bar soaps, creams, lotions, and gels. Typically, these products must satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and should not leave the skin or hair overly dry after frequent use. Further, cleansing compositions, particularly shampoos, designed for use with children should exhibit mildness to the ocular mucosae, and no or minimal eye sting, should material from the cleansing composition be placed in the eye.

It is highly desirable to deliver cleansing and conditioning benefits from a disposable substrate. Disposable products are convenient because they obviate the need to carry or store cumbersome bottles, bars, jars, tubes, and other forms of clutter associated with cleansing products and other products capable of providing therapeutic or aesthetic benefits. Disposable products are also a more sanitary alternative to the use of a sponge, washcloth, or other cleansing implement intended for extensive reuse, because such implements can develop bacterial growth, unpleasant odors, and other undesirable characteristics related to repeated use.

There is also a need for personal care articles, such as disposable washcloths, which can be easily used by young children. Such child-friendly personal care products must be easy to handle and the child must easily understand the method of utilizing them. Furthermore, any such products should ideally be suitable for use by consumers of different ages, e.g. children, sizes and/or stages of development.

This is especially true of so-called "one size fits all" wash mittens, such as a wash mitt which is suitable for children of all sizes. Typically, the products are designed to allow most users to be able to use the product. However, this effectively means a mitt which is far bigger than most user's hand a results in poor product performance and/or unintentional removal of the mitt during use. The alternative of providing a selection of sizes of mitts for different sized user's, while seemingly attractive, results in increased cost of producing, storing, delivering etc, the different sized mitts.

The need remains for disposable cleaning products, especially wash mitts, which are easy to use and suitable for use by consumers of different ages, size and/or stages of development, especially products which are suitable children of different ages.

SUMMARY OF THE INVENTION

A first aspect of the present invention provides, a disposable nonwoven cleansing mitt adapted to fit on a user's hand comprising:
(a) first and second substantially complementary nonwoven sheet members in an overlying relationship, the members defining an interior volume for receiving the user's hand, each of the first and second substantially complementary nonwoven sheet members including an exterior surface, having an opposing interior surface, a top edge, a bottom edge opposing the top edge, and first and second opposed side edges, the first and second substantially complementary nonwoven sheet members being secured to each other along the periphery of the top edge and both of said first and second opposed side edges, with the bottom edges being unsecured so as to provide an opening to the interior volume for inserting the user's hand therein, and at least one of the first and second sheet members comprises an adjustment means to permit a variation in the size of said interior volume, to accommodate different hand sizes; and
(b) a personal care composition, wherein at least one of the first and second sheet members is releasably carrying the personal care composition.

A second aspect of the present invention provides, a disposable nonwoven cleansing mitt adapted to fit on a child's hand comprising:
(a) first and second substantially complementary nonwoven sheet members in an overlying relationship, the members defining an interior volume for receiving the child's hand, each of the first and second substantially complementary nonwoven sheet members including an exterior surface, having an opposing interior surface, a top edge, a bottom edge opposing the top edge, and first and second opposed side edges, the first and second substantially complementary nonwoven sheet members being secured to each other along the periphery of the top edge and both of said first and second opposed side edges, with the bottom edges being unsecured so as to provide an opening to the interior volume for inserting the child's hand therein, and at least one of said first and second sheet members is a stretch laminate and provides for adjustment to permit a variation in the size of said interior volume, to accommodate different hand sizes; and
(b) a personal care composition, wherein at least one of the first and second sheet members is releasably carrying the personal care composition.

A third aspect of the present invention provides, a disposable nonwoven cleansing mitt adapted to fit on a user's hand comprising:
(a) first and second substantially complementary sheet members in an overlying relationship, the members defining an interior volume for receiving the user's hand, each of the first and second substantially complementary sheet members including an exterior surface, having an opposing interior surface, a top edge, a bottom edge opposing said top edge, and first and second opposed side edges, said first and second substantially complementary sheet members being secured to each other along the periphery of the top edge and both of the first and second opposed side edges, with the bottom edges being unsecured so as to provide an opening to the interior volume for inserting the user's hand therein, at least one of the first and second sheet members comprises an adjustment means to permit a variation in the size of the interior volume, to accommodate different hand sizes, wherein the first sheet member is a nonwoven sheet member and the second sheet member is a polymeric film; and (b) a personal care composition, wherein the first sheet member is releasably carrying the personal care composition.

All documents cited are, in relevant part, incorporated herein by reference; the citation of any document is not to be construed as an admission that it is prior art with respect to the present invention.

It should be understood that every limit given throughout this specification will include every lower, or higher limit, as the case may be, as if such lower or higher limit was expressly written herein. Every range given throughout this specification will include every narrower range that falls within such broader range, as if such narrower ranges were all expressly written herein.

All percentages, ratios and proportions are by weight, and all temperatures are in degrees Celsius (° C.), unless otherwise specified. All measurements are in SI units unless otherwise specified.

BRIEF DESCRIPTION OF THE DRAWINGS

The above-mentioned and other features and objects of this invention and the manner of attaining them will become more apparent, and the invention itself will be better understood by reference to the following description of the invention taken in conjunction with the accompanying drawings, wherein.

DETAILED DESCRIPTION

The instant articles, and methods of the present invention are suitable for use by a user, such as an adult and/or a child, in personal cleansing. Due to the ease and simple method of use very young children are able to clean themselves, to an extent independently, with the instant invention.

Definitions

As used herein the abbreviation "gsm" means "grams per square meter".

As used herein, "disposable" is used in its ordinary sense to mean an article that is disposed or discarded after a limited number of usage events, preferably 2 or less, and more preferably a single usage event.

As used herein "paste" or "paste form" means a composition of semisolid consistency.

The term "releasably carrying" means that a composition is contained in and/or on a nonwoven sheet member of the cleansing mitt and is readily releasable from the nonwoven member by application of water and/or application of some force to the cleansing mitt and/or the nonwoven sheet member, for example, wringing the nonwoven sheet member, wiping a child, or immersing the nonwoven sheet member or the entire cleansing mitt in water.

As used herein, the term "comprising" means that the various components, ingredients, or steps, can be conjointly employed in practicing the present invention. Accordingly, the term "comprising" is open-ended and encompasses the more restrictive terms "consisting essentially of" and "consisting of." Other terms may be defined as they are discussed in greater detail herein.

Figure 1:
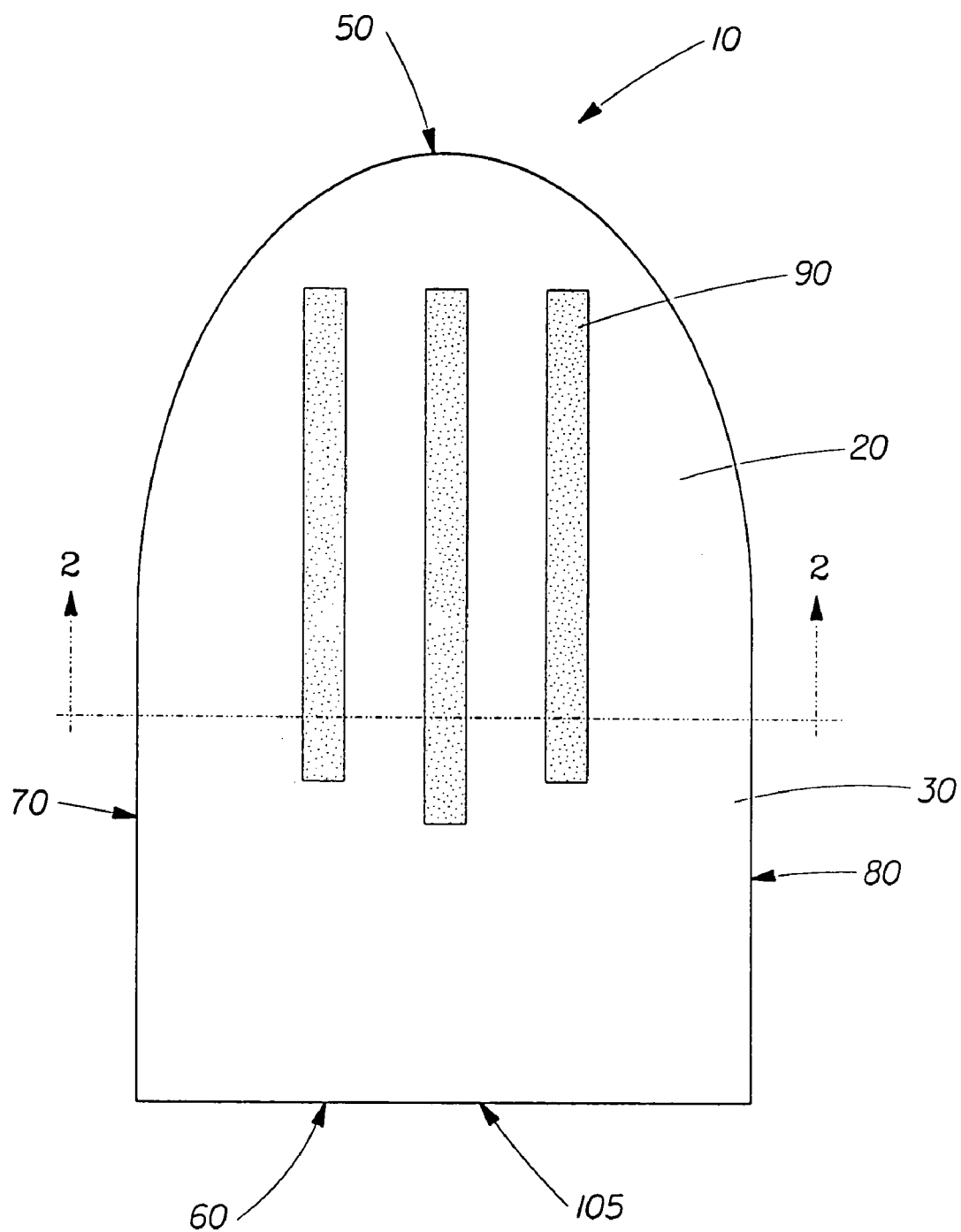
FIG. 1 illustrates a bottom plan view of one embodiment of a disposable nonwoven cleansing mitt.

Referring to FIG. 1, there is illustrated one possible embodiment of a disposable nonwoven cleansing mitt 10, in accordance with the present invention. The mitt 10 comprises a first nonwoven sheet member 20, which has an exterior surface 30, an interior surface 40 (FIGS. 4-6), a top edge 50, a bottom edge 60, a first side edge 70 and a second side edge 80. The first nonwoven sheet member 20, together with the complementary second nonwoven sheet member 110 (FIG. 2), which are in an overlying relationship, define an interior volume 100 (FIGS. 4-6) which is accessed by the user's hand via opening 105.

The cleansing mitt 10 also comprises a personal care composition 90. The first nonwoven sheet member 20 is releasably carrying a personal care composition 90. In one embodiment of the present invention the personal care composition 90 may be present on a part of the first nonwoven sheet member 20, such as, but not limited to, the exterior surface 30 in the form of stripes (as shown in FIG. 1), spots, geometric patterns, non-geometric patterns or in a random distribution. In an alternative embodiment, the personal care composition 90 may be present on the entire exterior surface 30 of the first nonwoven sheet member 20. In another an alternative embodiment the personal care composition 90 may be present in the interior of the first nonwoven sheet member, and/or the exterior surface of the nonwoven sheet member.

It is to be understood that while in FIG. 1 the exterior surface 30 of the first nonwoven sheet member 20 is releasably carrying the personal care composition 90 in other embodiments of the present invention the second nonwoven sheet member may be releasably carrying the personal care composition. There is no restriction as to which of the first nonwoven sheet member and the second nonwoven sheet member is releasably carrying the personal care composition. It is even possible that both the first and second nonwoven sheet members be releasably carrying the personal care composition. Furthermore, the personal care composition may be carried on the exterior surface, interior, and/or interior surface of any nonwoven member as long as a nonwoven member is releasably carrying it.

Figure 2:
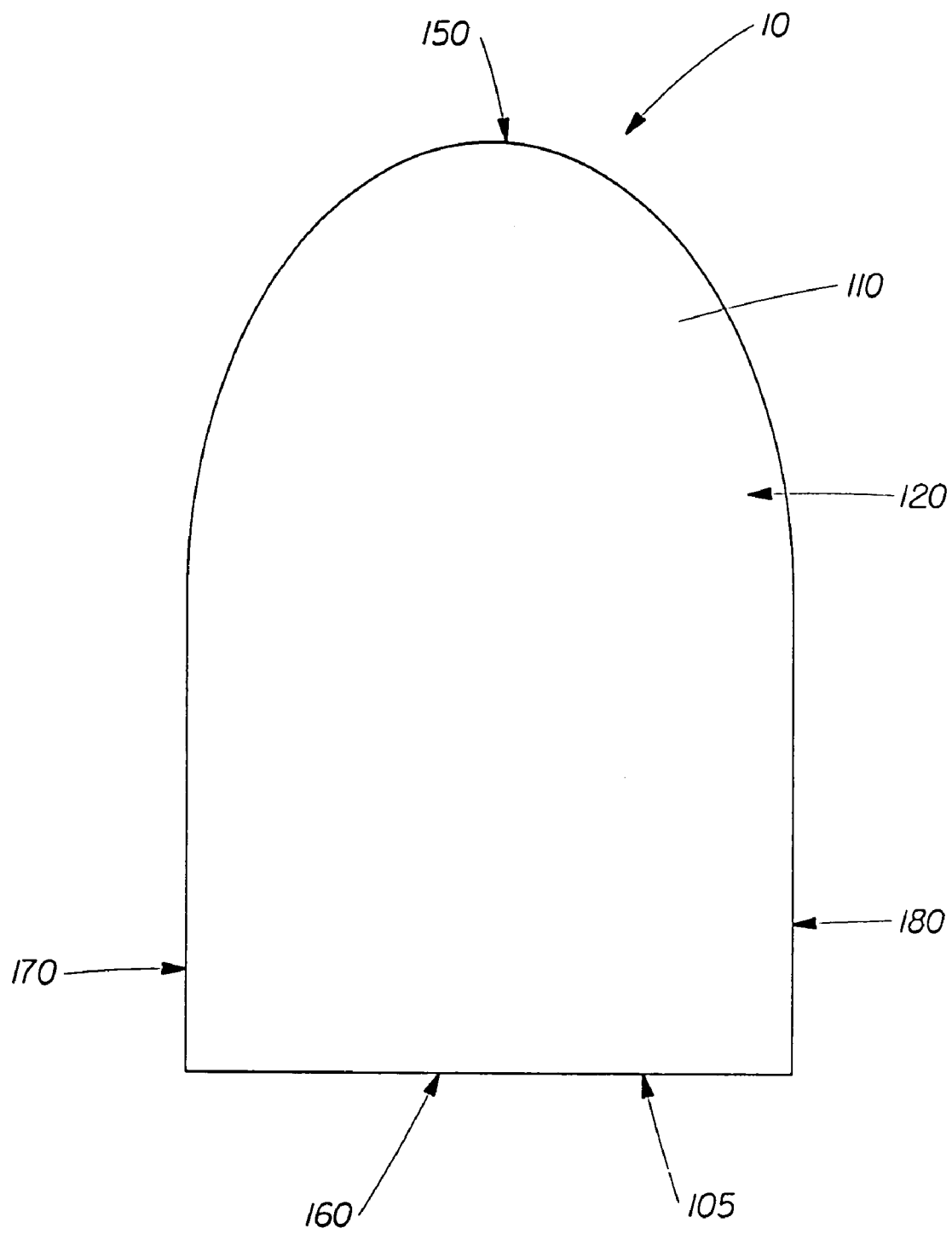
FIG. 2 illustrates a top plan view of the cleansing mitt of FIG. 1.

Referring to FIG. 2, there is illustrated a top plan view of the mitt 10 of FIG. 1. The mitt 10 comprises a second nonwoven sheet member 110, which has an exterior surface 120, an interior surface 130 (FIGS. 4-6), a top edge 150, a bottom edge 160, a first side edge 170 and a second side edge 180.

Figure 3:
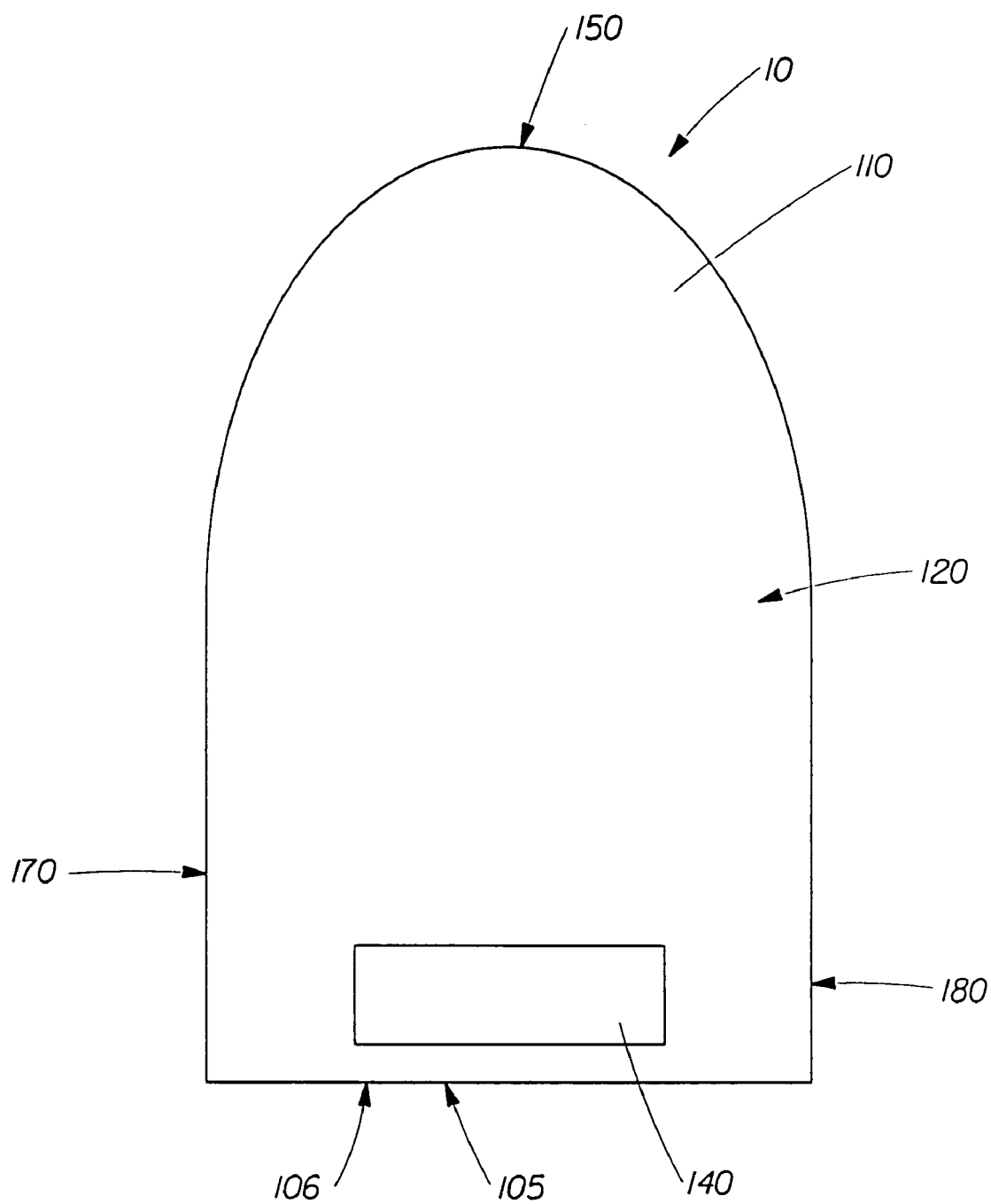
FIG. 3 illustrates an alternative top plan view of the mitt of FIG. 1.

Referring to FIG. 3, there is illustrated an alternative a top plan view of the mitt 10 of FIG. 1. The second nonwoven sheet member 110 has an adjustment means 140 to permit a variation in the size of the interiorly defined volume, to snugly accommodate different user's hand sizes. The adjustment means may be any means suitable for permitting a variation in the size of an interiorly defined volume, to snugly accommodate different hand sizes. Suitable adjustment means, include but are not limited to, include, hook and loop fasteners such as Velcro® and the like, elastic members, elastic strands, draw strings, gussets, cinches, buttons, fasteners, tabs, tongue and grove fasteners such as "ZIP-LOCK" type fasteners, resealable tape, belts, clips, adhesives, such as refastenable adhesives, and combinations thereof. Adjustment means, such as hook and loop fasteners, tabs, draw strings, tongue and grove fasteners, resealable tape, belts, clips, adhesives and the like, are adjusted by the user or a third party to increase or decrease the interior volume 100 (FIGS. 4-6) of the mitt 10. For adjustment means, such as elastic members, elastic strands, gussets and the like, increases or decreases the interior volume 100 (FIGS. 4-6) of the mitt 10 upon insertion of the user's hand.

In one optional embodiment of the present invention the adjustment means is on either the first nonwoven sheet member or the second nonwoven sheet member while the personal care composition is on the nonwoven sheet member not containing the adjustment means. In an alternative embodiment the personal care composition may be present on the same nonwoven sheet member as the adjustment means. However, while this alternative embodiment of both the first and second nonwoven sheet members releasably carrying the personal care composition is within the scope of the present invention, it is not preferred.

It is to be understood that while in FIG. 3 the adjustment means 140 on the second nonwoven sheet member 110, in other embodiments of the present invention the adjustment means may be present on the first nonwoven sheet member 20. There is no restriction as to which of the first nonwoven sheet member and the second nonwoven sheet member has the adjustment means.

Figure 4:
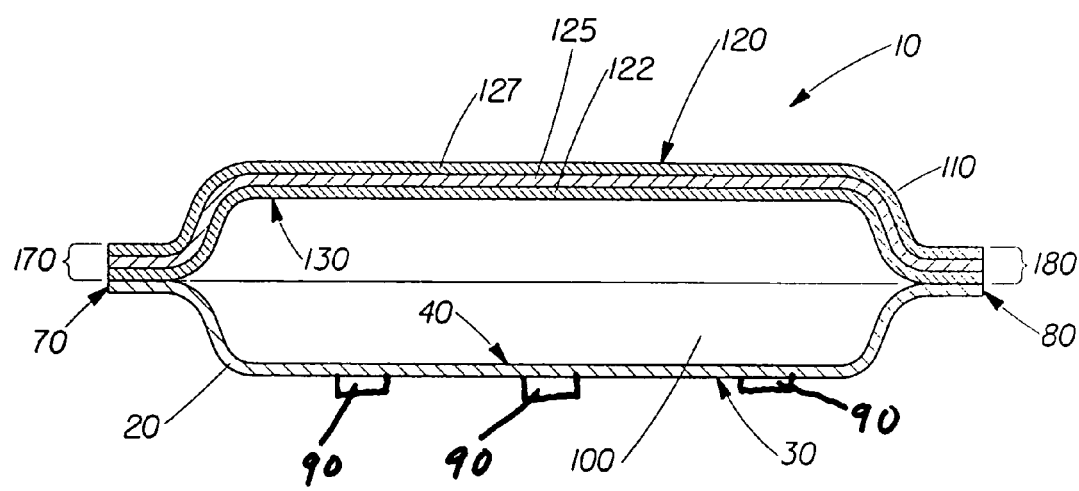
FIG. 4 is a sectional view along 2-2 of one alternative embodiment of the mitt of FIG. 1.

FIG. 4 shows a section view along 2-2 of one alternative embodiment of the cleansing mitt of FIG. 1. In FIG. 4 the first nonwoven sheet member 20 is a single layer material, typically a nonwoven material, preferably a high loft batting material which is explained in more detail herein. The first nonwoven sheet member 20 is also releasably carrying the personal care composition which is evenly distributed throughout the first nonwoven sheet member 20.

In FIG. 4 the second nonwoven sheet member 110 is a laminate having three layers 122, 125 and 127. Layers 122 and 127 may be the same or different and are typically a nonwoven material, preferably a nonwoven material with good softness. Suitable nonwovens, including those having good softness, are illustrated in more detail herein. Layer 125 is an elastic web, which is explained in more detail herein. Layer 125 together with layers 122 and 127 form a stretch laminate which permits a variation in the size of the interior volume 100, and act as an adjustment mechanism to accommodate, preferably snugly accommodate, different user's hand sizes.

Figure 5:
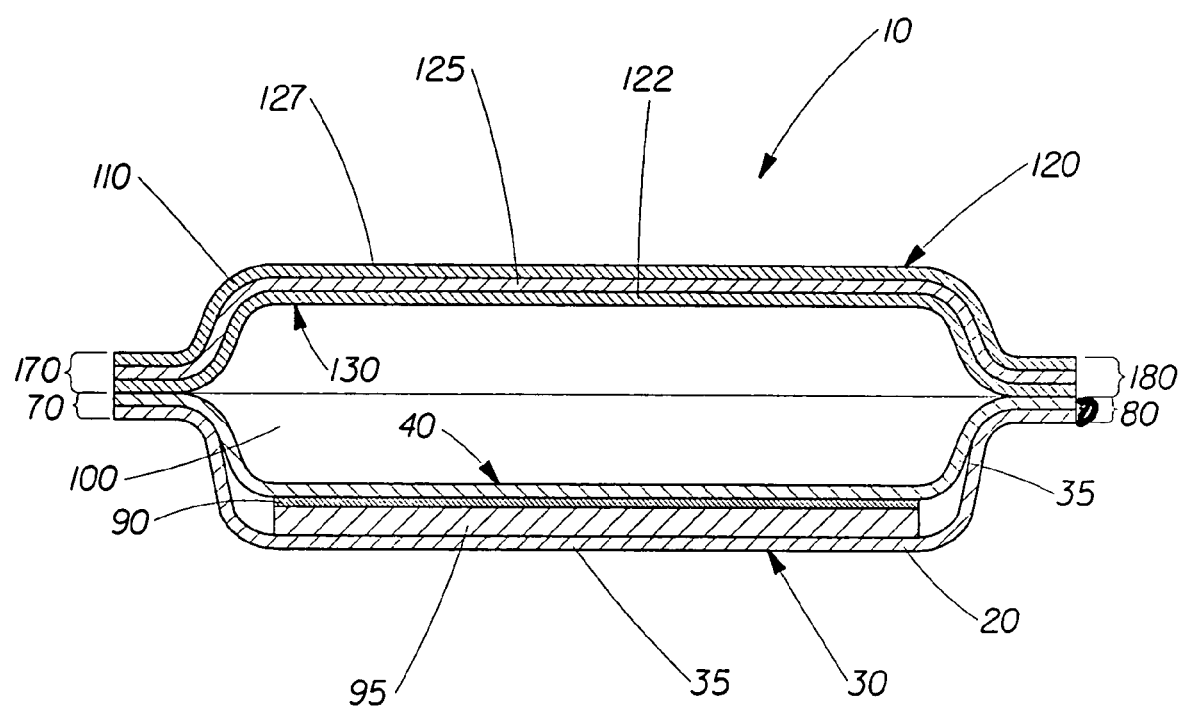
FIG. 5 is a sectional view of another alternative embodiment of the mitt of FIG. 1.
Figure 6:
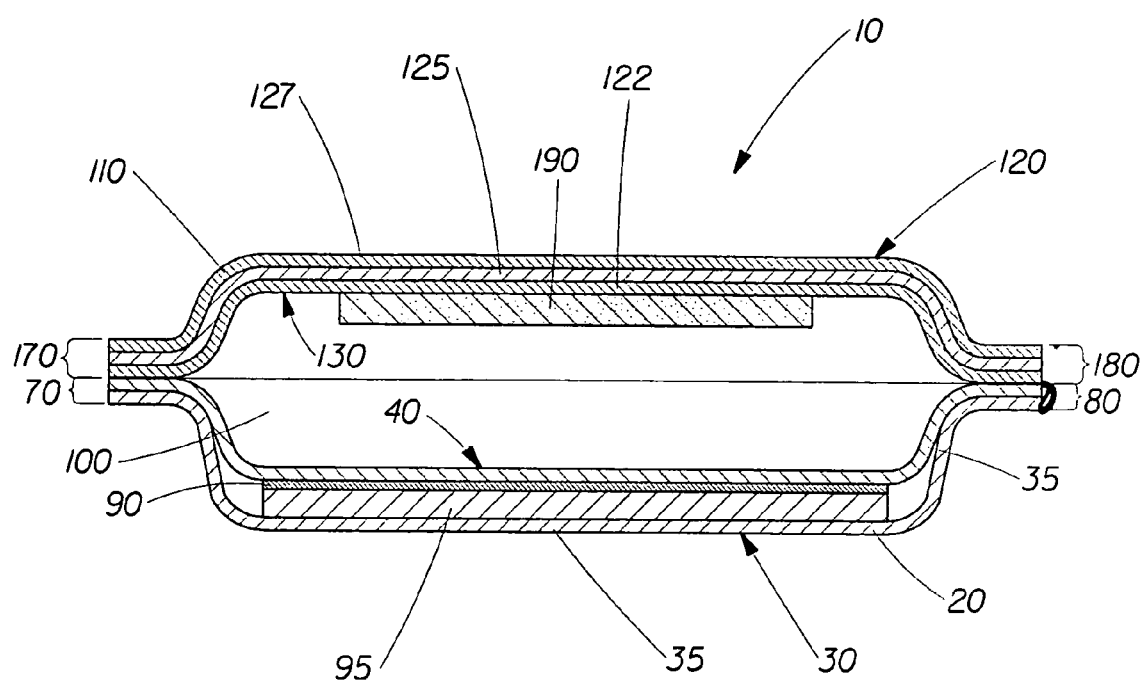
FIG. 6 is a sectional view of yet another alternative embodiment of the mitt of FIG. 1.

FIGS. 5 and 6 are sectional views along 2-2 showing a section view of two alternative embodiments of the cleansing mitt of FIG. 1. The second nonwoven sheet member 110 is a laminate having three layers 122, 125 and 127, and is the same as the laminate illustrated previously in FIG. 4. The first nonwoven sheet member 20 is a laminate having three layers. In first nonwoven sheet member 20 layer 35 is folded around layer 95 in a "C-like" fold, thereby forming the three-layer laminate. Layer 35 is typically a nonwoven material, preferably a nonwoven with good softness. Suitable nonwovens, including those having good softness, are illustrated in more detail herein. Layer 95 is typically a nonwoven material, preferably a high loft batting material, which is explained in more detail herein.

In FIGS. 5 and 6 the first nonwoven sheet member 20 is also releasably carrying the personal care composition 90, which is on a surface of layer 95 nearest to the interior surface 40 of the second nonwoven sheet member 20. In effect the personal care composition 90 is in the interior of the first nonwoven sheet member 20.

In an alternative embodiment of the present invention the one or both of the nonwoven sheet members are selected such that they, preferably their interior surface, will adhere, cling or stick to the child's hand prior to and during use. This optional adhesion may be achieved in a variety of ways, including, but not limited to, adhesive, friction, electrostatic attraction, conformation of the nonwoven sheet member to the shape of the child's hand when wet, and combinations thereof.

In one optional embodiment of the present invention the cleansing mitts include a retaining aid. The retention of the cleansing mitts on the user provides the user with additional confidence that the mitt will not fall off during use, especially during vigorous scrubbing. This means the consumer can focus on the task at hand, namely washing and cleaning, without having to be concerned with retaining the cleansing mitt on their hand.

FIG. 6 is one illustrative example of a mitt 10 containing a retaining aid, in the form of a polyolefin film 190 is attached to the interior surface 130 of the second nonwoven sheet member 110. Examples of suitable polyolefin films include, but are not limited, films comprising polyethylene and/or polypropylene, and the like. In FIG. 6 the polyolefin film is shown as a discrete swatch or patch, however in alternative embodiments the polymeric film may have substantially the same size and/or shape as the nonwoven member to which it is attached.

In another optional embodiment the retaining aid may be a tacky material, such as an adhesive, may be placed on the interior surface of one or both of the first and second nonwoven sheet members increasing the coefficient of friction between the skin on the user's hand and the disposable nonwoven cleansing mitt. This tacky material could be sprayed, printed or the like in the form of dots or other patterns.

Additional information on retaining aids and cleansing mitt containing them may be found in copending U.S. Provisional Patent Application No. 60/453,166 filed on Mar. 10, 2003, entitled "Disposable Nonwoven Cleansing Mitt" in the name of Benjamin et al.,.

Figure 7:
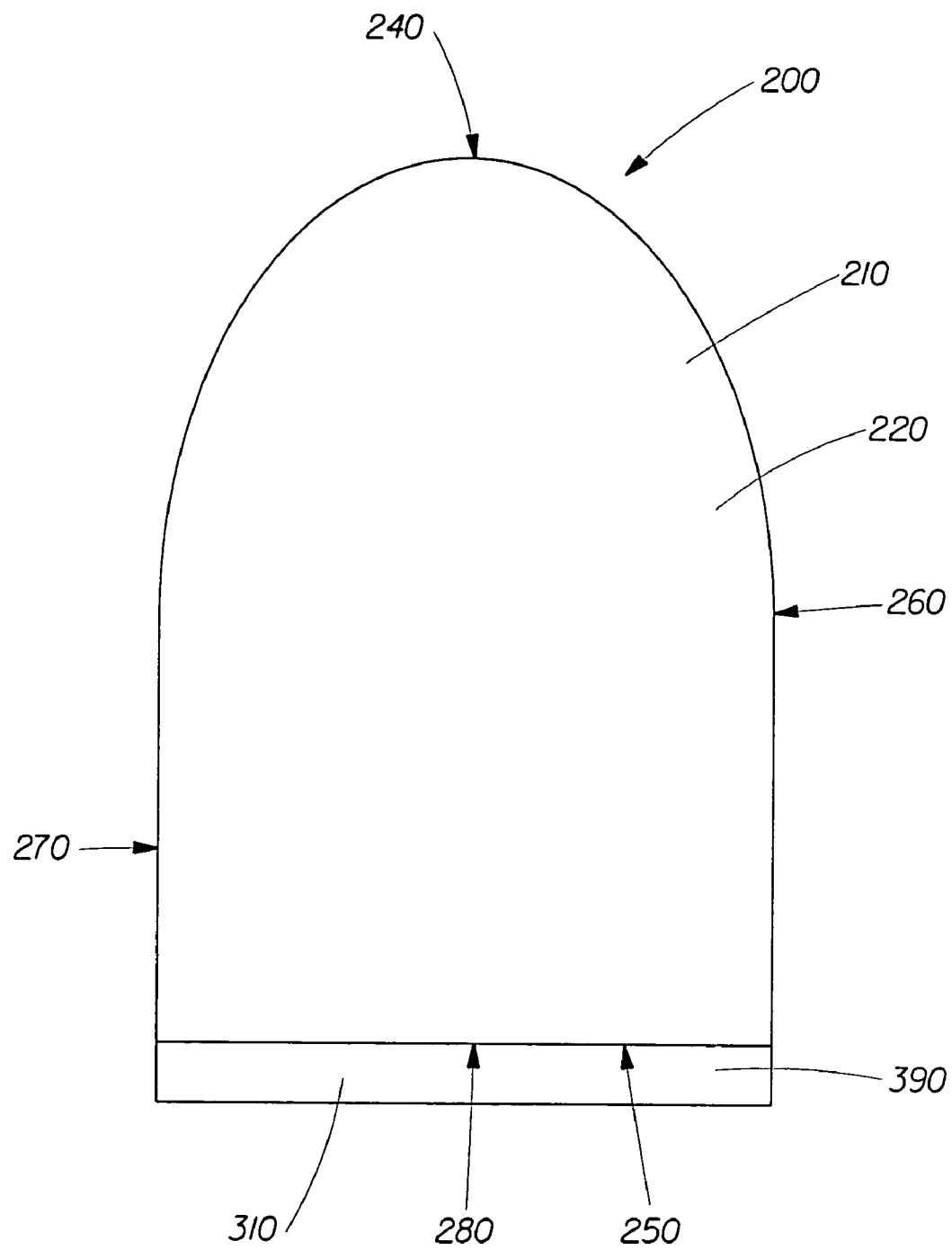
FIG. 7 illustrates a bottom plan view of another embodiment of a disposable nonwoven cleansing mitt.

Referring to FIG. 7, there is illustrated another one possible embodiment of a cleansing mitt 200, in accordance with the present invention. The cleansing mitt 200 comprises a first nonwoven sheet member 210, which has an exterior surface 220, an interior surface, a top edge 240, a bottom edge 250, a first side edge 260 and a second side edge 270. The first nonwoven sheet member 210, together with the substantially complementary second nonwoven sheet member 310, which are in an overlying relationship, define an interior volume which is accessed by the hand via 280. However, in this alternative embodiment the second nonwoven sheet member 310 is slightly longer than the first nonwoven sheet member 310 giving rise to an extension portion or tab 390. While not wanting to be limited by theory, this optional tab 390 is believed to provide a visual clue as to how a user, such as a child, can access the interior volume while also providing assistance in separating the first and second members.

Figure 8:
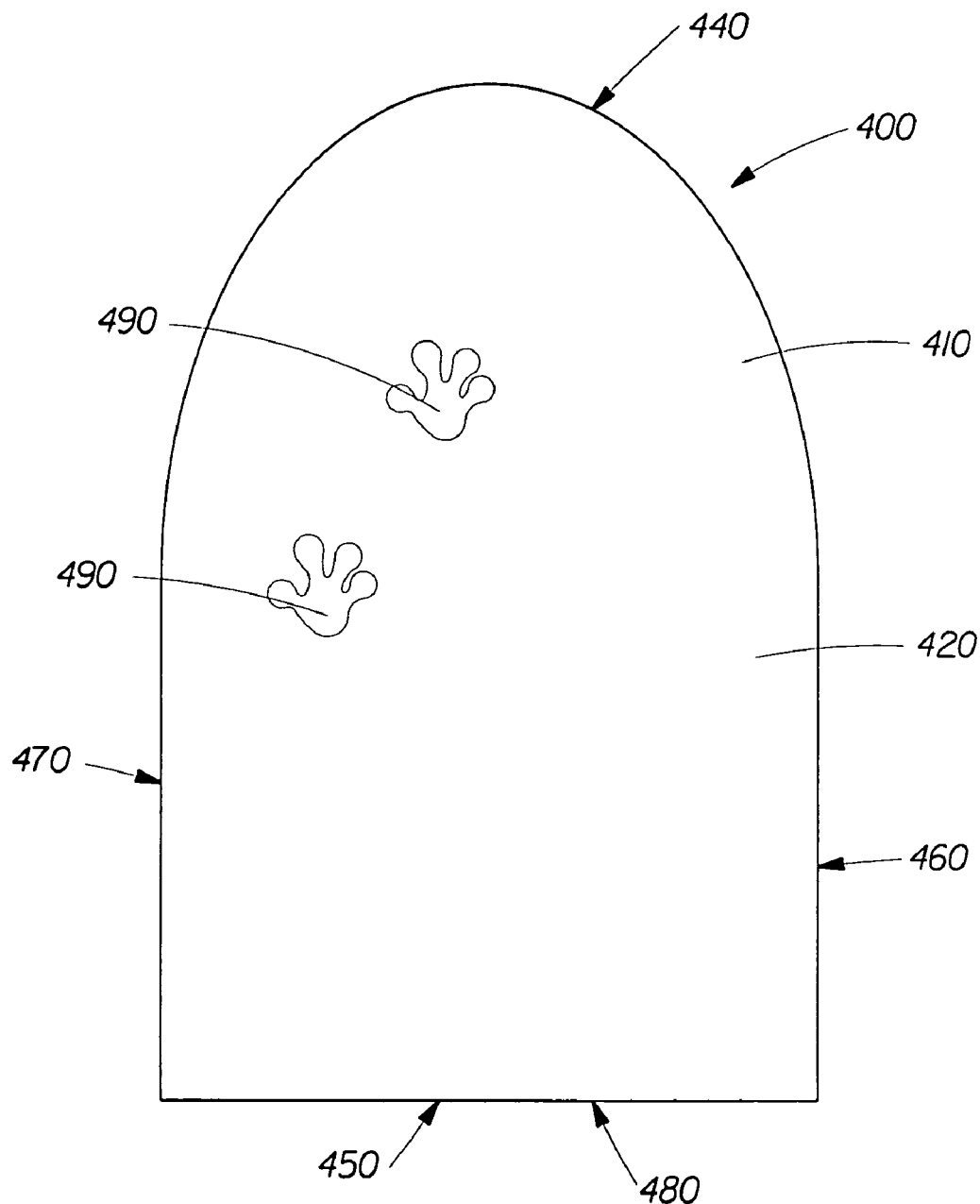
FIG. 8 illustrates a bottom plan view of another embodiment of a disposable nonwoven cleansing mitt.

Referring to FIG. 8, there is illustrated another possible embodiment of a cleansing mitt 400, in accordance with the present invention. The cleansing mitt 400 comprises a first nonwoven sheet member 410, which has an exterior surface 420, an interior surface, a top edge 440, a bottom edge 450, a first side edge 460 and a second side edge 470. The first nonwoven sheet member 410, together with the complementary second nonwoven sheet member, which are in an overlying relationship, define an interior volume which is accessed by the user's hand, such as a child's hand, via 480. The first nonwoven sheet member 410 has on its exterior surface 420 decorative matter 490. This printed matter may be of any size, shape, arrangement, color etc. It may be designs, symbols, characters, indicia and the like.

In one optional embodiment of the present invention one of the first nonwoven sheet member or the second nonwoven sheet member is releasably carrying the personal care composition while the decorative matter is on the nonwoven sheet member not releasably carrying the personal care composition.

In an alternative embodiment decorative matter is on both the first and second nonwoven sheet members. In another alternative embodiment decorative matter is on the same nonwoven sheet members as the personal care composition. However, while these two alternative embodiments are within the scope of the present invention, they are not preferred.

It is to be understood that while in FIG. 8 the decorative matter 490 on the exterior surface 420 of the first nonwoven sheet member 410, in other embodiments of the present invention the decorative matter, when present, may be on the second nonwoven sheet member. There is no restriction as to which of the first nonwoven sheet member and the second nonwoven sheet member has the decorative matter, when present. Furthermore, there is no restriction as to where on the first and/or second nonwoven sheet member the decorative matter is located, such as, on the exterior surface, interior, and/or interior surface of a nonwoven sheet member.

The manufacture of nonwoven sheet substrate per se forms no part of this invention.

The material of which nonwoven sheet members are made from should be strong enough to resist tearing during normal use, yet still provide softness to the user's skin, such as a child's tender skin. Additionally, the material should be water insoluble, or at least capable of retaining its form for the duration of the user's cleansing experience.

In one embodiment of the instant invention the nonwoven sheet members are a mixture of natural fibers and synthetic fibers. In alternative embodiments of the present invention the nonwoven sheet members may wholly comprise natural fibers, while in other alternative embodiments still may wholly comprise synthetic fibers.

In one embodiment of the present invention each nonwoven sheet member is made of material which is different to that of the other nonwoven sheet member. In another alternative embodiment of the present invention the two nonwoven sheet members are made of the same material.

Suitable natural fibers include but are not limited to cellulosic fibers, such as wood pulp fibers, cotton, and rayon. Suitable synthetic fibers include fibers commonly used in textiles, including but not limited to polyester (e. g. polyethylene terephthalate) and polypropylene fibers polyethylene, polyether, and combinations thereof. It is also possible to use bicomponent fibers, or simply bicomponent or sheath polymers. These bicomponent fibers can be used as a component fiber of the nonwoven sheet member, and/or they may be present to act as a binder for the other fibers present in the nonwoven material. Suitable nonwovens with good softness include, but are not limited to, nonwoven materials comprising polypropylene, polyethylene, cellulose, rayon, polyether, PET, bicomponent polymers, and combinations thereof.

Various forming methods can be used to form the nonwoven sheet members for use in the present invention. For instance, the nonwoven sheet members can be made by nonwoven dry forming techniques, such as air-laying, or alternatively by wet laying, such as on a papermaking machine, of a continuous web out of which the nonwoven sheet members are made. Other nonwoven manufacturing techniques, including but not limited to techniques such as adhesive bonding, melt blown, spunbonded, carding, needle punched, hydroentanglement and lamination methods may also be used. Combination of these methods may also be used.

The nonwoven sheet members of the present invention may be subjected to various treatments, such as, but not limited to, physical treatment, such as zone activation, ring rolling SELFing and the like; chemical treatment, such as, rendering part or all of the nonwoven sheet member hydrophobic, and/or hydrophilic, and the like; thermal treatment, such as softening of fibers by heating, thermal bonding and the like; and combinations thereof.

In one embodiment of the present invention the nonwoven sheet members may comprise a high loft batting material. High loft batting material is a low density, as compared to similar non-high loft nonwoven material, nonwoven comprising a random array of void spaces throughout its structure. High loft batting material is sponge like in its structure and appearance. While not wanting to be limited by theory, it is believed that when the nonwoven sheet member comprises high loft batting material and is releasbly carrying the personal care composition there is superior foam generation, such as but not limited to, quality, volume duration etc., compared to a non-high loft batting nonwoven.

In one embodiment of the present invention one of the nonwoven sheet members is a high loft batting material having a basis weight of from about 50 gsm to about 80 gsm. An example of one suitable nonwoven high loft batting material is a 60 gsm polyester nonwoven, Proef 1297 available from Libeltex of Meulebeke Belgium.

In one embodiment, the nonwoven sheet members may be an airlaid nonwoven material comprising a combination of natural fibers, staple length synthetic fibers and a latex binder. The nonwoven material can be about 20-80 percent by weight wood pulp fibers, 10-60 percent by weight staple length polyester fibers, and about 10-25 percent by weight binder.

Additional information on materials which are suitable for use as the nonwoven sheet members of the present invention can be found in the following patents: U.S. Pat. No. 3,862,472 issued Jan. 28, 1975; U.S. Pat. No. 3,982,302 issued Sep. 28, 1976; U.S. Pat. No. 4,004,323 issued Jan. 25, 1977; U.S. Pat. No. 4,057,669 issued Nov. 8, 1977; U.S. Pat. No. 4,097,965 issued Jul. 4, 1978; U.S. Pat. No. 4,176,427 issued Dec. 4, 1979; U.S. Pat. No. 4,130,915 issued Dec. 26, 1978; U.S. Pat. No. 4,135,024 issued Jan. 16, 1979; U.S. Pat. No. 4,189,896 issued Feb. 26, 1980; U.S. Pat. No. 4,207,367 issued Jun. 10, 1980; U.S. Pat. No. 4,296,161 issued Oct. 20, 1981; U.S. Pat. No. 4,309,469 issued Jan. 25, 1982; U.S. Pat. No. 4,682,942 issued Jul. 28, 1987; and U.S. Pat. Nos. 4,637,859; 5,223,096; 5,240,562; 5,556,509; and 5,580,423.

In one embodiment of the present invention one of the nonwoven sheet members comprises a first material, typically a nonwoven material, which is joined to an elastic web to form a two-layer laminate. In another embodiment of the present invention one of the nonwoven sheet members is a three-layer laminate of two nonwoven materials, forming the outer layers, with an elastic web sandwiched between the nonwoven materials.

When the nonwoven sheet member is a laminate containing one or more layers of nonwoven materials and optionally, one or more layers of elastic web, the nonwoven materials and the elastic web can be joined to one another in surface-tosurface relationship, either at several intermittent points of surface contact or substantially continuously over at least a portion of their coextensive surfaces to form the nonwoven sheet member. The elastic web can be in either a tensioned or an untensioned condition, but preferably the nonwoven material is joined with the elastic web while the elastic web is in a substantially untensioned condition.

The elastic web can be made from any suitable elastomeric material. Generally, any suitable elastomeric resins, or blends containing such resins, can be utilized for forming the elastomeric web. For example, the elastic web can be an elastomeric film made from block copolymers having the general formula A-B-A', where A and A' are each a thermoplastic polymer endblock that contains a styrenic moiety, such as a poly(vinyl arene) and where B is an elastomeric polymer midblock, such as a conjugated diene or a lower alkene polymer. Other suitable elastomeric webs, for example, can include polyurethane elastomeric materials, such is those available from B.F. Goodrich & Company of Cleveland, Ohio under the trademark ESTANE, those employing polyamide materials available from Elf Atochem of Philadelphia, Pa. under the trademark PEBAX, and polyester materials available from E.I. duPont de Nemours & Company of Wilmington, Del. under the trademark HYTREL.

A polyolefin can also be blended with an elastomeric resin to improve the processability of the combination. The polyolefin must be one that is extrudable, in blended form, along with the elastomeric resin. Useful blending polyolefin materials include polyethylene, polypropylene, and polybutene, as well as ethylene copolymers, polypropylene copolymers, and butene copolymers.

The elastomeric web can also be a pressure-sensitive elastomeric adhesive web. For example, the elastomeric web can itself be tacky or, alternatively, a compatible tackifying resin can be added to the extrudable elastomeric compositions described above, to provide an elastomeric web that can act as a pressure-sensitive adhesive to bond the elastomeric web to a nonwoven material to for a nonwoven sheet member. The elastomeric web can also be a multilayer material that can include two or more individual coherent webs or films. Additionally, the elastomeric web can be a multilayer material in which one or more layers contains a mixture of elastic and inelastic fibers or particles.

Other suitable elastomeric materials for use as the elastomeric web include "live" synthetic or natural rubber, elastomeric polyolefin metallocene catalyzed materials, heat-shrinkable elastomeric films, elastomeric strands, formed elastomeric scrim, elastomeric foams, or the like.

In another alternative embodiment of the present invention the nonwoven sheet member is a laminate containing one or more layers of nonwoven materials and one or more layers of film. Examples of such optional films, include, but are not limited to, polyolefin films, such as, polyethylene film. An illustrative, but non-limiting example of a nonwoven sheet member which is a laminate is a laminate of a 16 gsm nonwoven polypropylene and a 0.8 mm 20 gsm polyethylene film.

In one alternative embodiment, the nonwoven sheet members can each comprise a hydroentangled material having a basis weight of about 62 grams per square meter and comprising about 50 percent by weight rayon fibers and about 50 percent by weight polyester fibers, polypropylene fibers, or a combination thereof. In another alternative embodiment, the nonwoven sheet members can comprise a laminate of two outer hydroentangled materials, such as nonwoven material of polyester fibers having a basis weight of about 30 grams per square meter, joined to an inner constraining layer, which can be in the form of net-like scrim or a continuous plastic film material which contracts upon heating to provide surface texture in on the outer hydroentangled materials.

In one embodiment of the present invention the surface of nonwoven sheet members is essentially flat. In another embodiment of the present invention the surface of the nonwoven sheet members may optionally contain raised and/or lowered portions. These can be in the form of logos, indicia, trademarks, geometric patterns, images of the surfaces that the cleansing mitt is intended to clean (i.e., infant's body, face, etc.). They may be randomly arranged on the surface of the nonwoven sheet member or be in a repetitive pattern of some form. They may be on one or both of the nonwoven sheet members. In one embodiment one of the nonwoven sheet members contains a repetitive pattern or alternating raised and lowered portions of the substrate. This variation in or on the surface of the nonwoven sheet members may be included to convey to the user, such as a child or a caregiver information on the cleansing mitt intended use, how a user, such as a child, is to place the mitt on the their hand, which brand or type of cleansing mitt they are using is or even to aid in cleaning of the user.

It is also within the scope of the present invention that the nonwoven sheet member includes laminates of two or more materials. Commercially available laminates, or purposely built laminates would be within the scope of the present invention. The laminated materials may be joined or bonded together in any suitable fashion, such as but not limited to, ultrasonic bonding, adhesive, glue, fusion bonded, heat or thermal bonded and combinations thereof. One such suitable commercially available laminate is 259-50-3 available from Tredegar of Richmond, Va. U.S.A.

In another embodiment of the present invention the nonwoven sheet members are biodegradable. For example the substrate could be made from a biodegradable material such as a polyesteramide, or a high wet strength cellulose.

The first and second complementary nonwoven sheet members may be joined or bonded together in any suitable fashion. For example, the first and second nonwoven sheet members may be joined by ultrasonically bonding, sewing, adhesively, mechanically bonding, fusion bonding, heat or thermal bonding and combinations thereof. The first and second nonwoven sheet members are joined at their respective first, second and top edges. The bottom edges may be either totally unbonded or partially bonded. Any such partial bond will not restrict a child from wearing the mitt, and may aid in securing the mitt to the child's hand.

The cleansing mitt can be manufactured in various sizes. One embodiment of the present invention include cleansing mitts in which the interior volume is divided into two parts, one part for the user's thumb and one part for the remainder of the user's hand. In an alternative embodiment the interior space is not divided and can contain the whole of the user's hand. This embodiment of the present invention is illustrated in the cleansing mitts of the Figures.

In one optional embodiments of the present invention the cleansing mitt will typically have dimensions which make it suitable for use by a child. That is the cleansing mitt 10 with a length, as measured between bottom end 60 and top end 50, of from about 100 mm to about 200 mm and a total width between sides 70 and 80 of from about 80 mm to about 125 mm. The opening to access the interior portion of the cleansing mitt is from about 20 mm to about 100 mm.

In another optional embodiment of the present invention is a child's cleansing mitt 10 with a length, as measured between bottom end 60 and top end 50, of about 155 mm, and a total width between sides 70 and 80 of about 105 mm. The opening to access the interior portion of the child's cleansing mitt is about 50 mm.

Personal Care Composition

The personal care compositions releasably carried by the disposable cleaning implement of the present invention may comprise a variety of components such as are conventionally used in personal care compositions. These optional components should be suitable for application to a child's skin and hair; that is, when incorporated into the article they are suitable for use in contact with human skin without undue toxicity, incompatibility, irritation, instability, allergic response, and the like, within the scope of sound medical or formulator's judgment.

In one embodiment of the present invention the personal care compositions are in the form of a paste, or a dry solid. While personal care compositions comprising more than about 50% by weight of the composition of a liquid carrier, such as water, are within the scope of the present invention, it is preferred that any disposable cleaning implement be mostly dry, more preferably dry to the touch, prior to contact with the washing environment, that is, until the child first immerses the disposable cleaning implement or otherwise contacts it with water. Typically, this translates into levels of liquid carrier, such as water, of less than or equal to about 10%, more preferably less than or equal to about 7% by weight of personal care composition.

In one alternative embodiment of the present invention the amount of personal care composition present in the disposable cleaning implement is preferably present in amounts from about 1 gsm to about 200 gsm, more preferably from about 10 gsm to about 175 gsm, even more preferably still from about 20 gsm to about 150 gsm. (Grams of personal care composition per square meter of nonwoven sheet member) Alternatively, each disposable cleaning implement may contain from about 1 g to about 20 g, more preferably from about 1 g to about 15 g of personal care composition per disposable cleaning implement.

Surfactants

The personal care compositions used in the present invention may optionally contain one or more surfactant. Typically the optional surfactant, when present, is selected from the group consisting of anionic surfactants, amphoteric surfactants, nonionic surfactants, zwitterionic surfactants, cationic surfactants, and mixtures thereof.

The surfactants of the personal care compositions may be lathering or non-lathering surfactants. As used herein, "lathering surfactant" means a surfactant, which when combined with water and mechanically agitated generates a foam or lather. A "nonlathering surfactant" produces no such foam or lather under similar conditions. It is preferred, however, that the surfactants be lathering since increased lather is important to consumers as an indication of cleansing effectiveness.

Nonlimiting examples of surfactants useful in the compositions of the present invention are disclosed in McCutcheon's, *Detergents and Emulsifiers*, North American edition (1986), published by Allured Publishing Corporation; McCutcheon's, *Functional Materials*, North American Edition (1992); and U.S. Pat. No. 3,929,678, to Laughlin et al., issued Dec. 30, 1975.

Some nonlimiting examples of suitable surfactants include ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium monolauryl phosphate, sodium cocoglyceryl ether sulfonate, sodium $C_9$-$C_{22}$ soap, amine oxides such as lauramine oxide and cocoamine oxide, decyl polyglucose, lauryl polyglucose, sucrose cocoate, $C_{12-14}$ glucosamides, sucrose laurate, fatty amines, di-fatty quaternary amines, tri-fatty quaternary amines, imidazolinium quaternary amines, PEG 80 Sorbitan laurate, PEG-150 distearate, sodium laureth-13 carboxylate, disodium lauroamphodiacetate, sodium lauroamphoacetate, cetyl dimethyl betaine, cocoamidopropyl betaine, cocoamidopropyl hydroxy sultaine, and combinations thereof.

Surfactant, when present, is typically employed in compositions at levels of preferably from about 0.01% to about 99%, more preferably from about 0.5% to about 97%, and more preferably from about 1.0% to about 98%, by weight of the personal care composition.

Adjunct Ingredients

The personal care compositions used in the present invention may optionally contain one or more adjunct ingredients.

The *CTFA Cosmetic Ingredient Handbook*, Second Edition (1992) describes a wide variety of nonlimiting cosmetic, neutraceutical, and pharmaceutical ingredients commonly used in the skin care industry, which are suitable for use as adjunct ingredients in the personal care compositions used in the present invention. Examples of these ingredient classes include, but are not limited to: enzymes, absorbents, aesthetic components, fragrances, pigments, colorings, colorants, essential oils, skin sensates, anti-acne agents (e.g., resorcinol, sulfur, salicylic acid, erythromycin, zinc, etc.), anti-caking agents, antifoaming agents, preservative, conditioners, hair conditioners, dye, antimicrobial agents (e.g., quaternium-15, methyl paraben, ethyl paraben, propyl paraben, DMDM hydantoin etc.), antioxidants, glycerin, binders, biological additives, buffering agents, bulking agents, chelating agents, chemical additives, solvents, cosmetic biocides, denaturants, external analgesics, film formers or materials, e.g., polymers, for aiding the film-forming properties and substantivity of the composition (e.g., copolymer of eicosene and vinyl pyrrolidone), humectants, opacifying agents, pH adjusters, process aids, reducing agents, sequestrants, skin-conditioning agents (humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, binders, thickeners, hydrocolloids, zeolites, and vitamins and derivatives thereof (e.g., tocopherol, tocopherol acetate, beta carotene, retinoic acid, retinol, retinoids, retinyl palmitate, niacin, niacinamide, and the like). The personal cleansing compositions releasably contained by the disposable cleaning implement may include carrier components such as are known in the art, for example water, alcohols, polyols, and the like. Such carriers can include one or more compatible liquid or solid filler diluents or vehicles which are suitable for application to skin or hair. Additionally, the adjunct ingredients can be applied to the nonwoven sheet member as a deposit separate from that of any optional surfactant deposited on the nonwoven sheet.

The adjunct ingredients useful herein can be categorized by their therapeutic or aesthetic benefit or their postulated mode of action. However, it is to be understood that the adjunct ingredients useful herein can in some instances provide more than one therapeutic or aesthetic benefit or operate via more than one mode of action. Therefore, classifications herein are made for the sake of convenience and are not intended to limit the component to that particular application or applications listed. Also, when applicable, the pharmaceutically-acceptable salts of the components are useful herein.

Adjunct ingredients, when present, are each typically employed in compositions at levels of from about 0.0001% to about 99.9%, preferably from about 0.001% to about 99%, and more preferably from about 0.01% to about 97%, by weight of the personal care composition.

In preparing the cleansing mitt of the present invention the personal care composition need to be releasably carried by at least one of the nonwoven sheet members. Techniques for combining the nonwoven sheet member with the personal care composition are well known in the art. Examples of common methods of combining the personal care composition with the nonwoven sheet member may involve coating, immersing, dipping, printing, and/or spraying, the nonwoven sheet member with the personal care composition of the present invention. The personal care composition of the present invention is added to the nonwoven sheet member at level sufficient to provide the desired benefits of the present invention. A convenient method of combining the personal care composition of the present invention with the chosen nonwoven sheet member is for the personal care composition to be applied to the nonwoven sheet member while the nonwoven sheet member is a continuous web. The application could be in many forms, including but not limited to one or more of, coating, immersing, dipping, spraying, printing, extruding and the like. Once the personal care composition is applied the nonwoven sheet, the member is cut to the desired length and then packaged for sale. Alternatively, the personal care composition may be added to a nonwoven sheet member when the nonwoven sheet member is part of a formed cleansing mitt.

The personal care composition may be added to the nonwoven sheet member to the nonwoven sheet member in any convenient fashion. For example, the personal care composition components could all be mixed together and then sprayed onto the nonwoven sheet member; each component could be deposited on the nonwoven sheet member separately; or half the components could be mixed together and then added to the nonwoven sheet member, with the remainder then being mixed together and then sprayed on to the nonwoven sheet member.

In one optional embodiment of the present invention the personal care composition is applied to the nonwoven sheet member, in the form of a paste prior to the assembly of the cleansing mitt. This optional embodiment is more preferably a "hot melt" composition. Hot melt composition have high viscosity at or around room temperature, and then melt (become substantially liquid) at higher temperatures. Such systems are advantageous during processing of a disposable, substantially dry (or dry to the touch) cleansing mitt since the composition can be applied (e.g., coated, sprayed, extruded) to the nonwoven sheet member at a low viscosity (e.g., a liquid) at higher than room temperature, and then as the composition cools down, it becomes a high viscosity paste or solid.

Article of Commerce

In one embodiment of the present invention an article of commerce is provided. The article of commerce of the present invention typically comprises (a) a container as described herein, and (b) at least one cleansing mitt as described herein.

Containers useful in the present article include but are not limited to, for example, PET tubs, flow wrap pouches, precut sachets for individually packed cleansing mitt, and other packaging known in the art as suitable for nonwoven article releasably carrying a composition. In one embodiment of the present invention the cleansing mitt of the present invention are stored in the containers which are water tight, water proof, water resistant, or the like, to reduce the possibility of accidental contact of with water of any of the cleansing mitts while in the container. Additionally, the container can also be manufactured to facilitate removal of individual cleansing mitts.

The container can be made of any suitable material or materials, and can be manufactured in any suitable manner. For example, the container can be made of polystyrene, polypropylene, PET, POET, polyethylene, polyester, polyvinyl alcohol, or the like. The containers may also be made of mixtures of materials. The containers can be manufactured by, for example, a vacuum molding process or an injection molding process, or any suitable process.

In one optional embodiment of the present invention the containers may also comprise hooks, suction cups or the like, which enable the container to be retained on, for example, the side of a bath tub, over a bathroom fixture, such as a shower head, faucet and the like, or even directly attached to the bathroom wall.

The disposable nonwoven cleansing mitts of the present invention may also be used in an article of commerce as described in copending U.S. Provisional Patent Application No. 60/453,167 filed on Mar. 10, 2003, entitled "Child's Cleansing System" in the name of Sanchez et al.,.

EXAMPLES

Example 1

A child's bathing mitt comprising a first member which is a 60 gsm polyester nonwoven high loft batting material, Proef 1297 available from Libeltex of Meulebeke Belgium, around and a second member which is a three member laminate. The three member laminate contains a 90 gsm two layer stretch laminate, namely 259-50-3 available from Tredegar of Richmond, Va. U.S.A., and a 30 gsm nonwoven, 008YLCO09U, available from BBA of Nashville Tenn., U.S.A. The high loft batting material is releasably carrying the personal care composition, which is 85 gsm of Miracare BC20, available from Rhodia of France.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. A disposable nonwoven cleansing mitt adapted to fit on a child's hand, said mitt comprising:
   (a) a first member configured as a laminate of three or more layers, said first member including a high loft batting material and a first nonwoven sheet; said nonwoven sheet being C-folded around said high loft batting material, said high loft batting material having a higher basis weight than said nonwoven sheet;
   (b) a second member configured as a laminate of two or more layers of material, at least one layer in said laminate being a nonwoven sheet, said first and second members being configured in an overlying relationship to define an interior volume for receiving said user's hand, each of said first and second members including an exterior surface, an opposing interior surface, a top edge, a bottom edge opposing said top edge, and first and second opposed side edges, said first and second members being secured to each other along the periphery of said top edges and said first and second opposed side edges, wherein at least a portion of said bottom edges are unsecured so as to provide an access opening to said interior volume for inserting said user's hand therein;
  (c) a retaining aid secured to the interior surface of at least one of said first and second members;
  (d) an adjustment means to permit a variation in the size of said interior volume, to accommodate different hand sizes; and
  (e) a personal care composition being releasably carried by said high loft batting material, said personal care composition including a lathering surfactant and less than about 10% water.

2. The cleansing mitt of claim 1, wherein the second member includes one or more layers of elastic web material.

3. The cleansing mitt of claim 2, wherein the second member is configured as a laminate comprising one or more layers of elastic material sandwiched between two layers of nonwoven material.

4. The cleansing mitt of claim 2, wherein the elastic material is a web of pressure-sensitive elastomeric material.

5. The cleansing mitt of claim 2, wherein the elastic material provides the adjustment means.

6. The cleansing mitt of claim 1, wherein at least one of the first and second members includes an inner constraining layer that has been contracted to provide surface texture to at least one of the first and second members.

7. The cleansing mitt of claim 1, further comprising at least one of raised and lowered portions on said exterior surface of at least one of said first and second members to aid in cleaning of said child.

8. The cleansing mitt of claim 1, wherein said retaining aid is a polyolefin film.

9. The cleansing mitt of claim 8, wherein said polyolefin film is a linear low-density polyethylene film.

10. The cleansing mitt of claim 1, wherein each of said first and second members independently comprise fibers selected from the group consisting of rayon, polypropylene, cellulose, polyesters, and mixtures thereof.

11. The cleansing mitt of claim 1, wherein said surfactant is selected from the group consisting of anionic surfactants, cationic surfactants, amphoteric surfactants, nonionic surfactants, zwitterionic surfactants and mixtures thereof.

12. The cleansing mitt of claim 1, wherein said personal care composition includes an adjuvant selected from the group consisting of enzymes, fragrances, pigments, essential oils, skin sensates, preservatives, conditioners, hair conditioners, carriers, dyes, antimicrobial agents, antioxidants, binders, buffering agents, chelating agents, solvents, film formers, humectants, glycerin, aloe vera, pantothenic acid, allantoin, bisabolol, dipotassium glycyrrhizinate, skin treating agents, binders, thickeners, hydrocolloids, vitamins and mixtures thereof.

13. An article of commerce comprising a container housing at least one disposable nonwoven cleansing mitt according to claim 1.

* * * * *